United States Patent [19]

Abraham

[11] Patent Number: 4,482,571
[45] Date of Patent: Nov. 13, 1984

[54] SICKLE CELL ANEMIA TREATMENT AND COMPOUND

[75] Inventor: Donald J. Abraham, Murrysville, Pa.

[73] Assignee: University of Pittsburgh, Pittsburgh, Pa.

[21] Appl. No.: 390,760

[22] Filed: Jun. 21, 1982

[51] Int. Cl.$^3$ ............................................. A61K 31/19
[52] U.S. Cl. ....................................... 424/317; 562/470
[58] Field of Search ........................ 424/317; 560/470

[56] References Cited

U.S. PATENT DOCUMENTS 3,262,850  7/1966  Jones et al. .......................... 424/317
4,062,974  12/1977  Coirault .............................. 424/308

OTHER PUBLICATIONS

National Library of Medicine, "Sickle Cell Anemia", Special Literature Search, Jan. 1970–Jun. 1974; Jul. 1974–Mar. 1978.
"Hemoglobin and the Sickling Cell", by Larry Varner, Pitt Capsule, pp. 4–18.

Primary Examiner—Frederick E. Waddell
Attorney, Agent, or Firm—Arnold B. Silverman

[57] ABSTRACT

A method of treating a person for sickle cell anemia including administering a therapeutically effective dosage of the compound

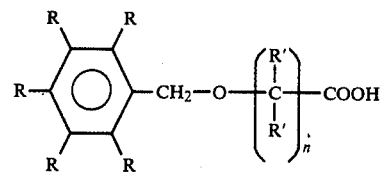

wherein at least one R=Cl, Br, $CH_3$ or $OCH_3$ and all the remaining R=H, R'=H or $CH_3$ and n=1, 2, 3, 4 or 5. Among the preferred species are p-bromobenzyloxyacetic acid, 2-(p-bromobenzyloxy)-2-methylpropionic acid and 3, 4 dichlorobenzyloxyacetic acid. The compound 2-(p-bromobenzyloxy)-2-methylpropionic acid or 3,4 dichlorobenzyloxyacetic acid. The same compound provided as a pharmaceutical in unit dosage form and having properties of resisting the aggregation of hemoglobin in a sickle cell anemia patient.

8 Claims, No Drawings

SICKLE CELL ANEMIA TREATMENT AND COMPOUND

BACKGROUND OF THE INVENTION

1. Field of the Invention

This invention relates to a method of treatment of sickle cell anemia and a compound having properties which resist sickling of hemoglobin in a sickle cell anemia patient.

2. Description of the Prior Art

Sickle cell anemia is a hereditary blood disease which afflicts members of the Negro race and, to a very limited extent, Caucasians of Mediterranean and mideastern ancestry. The anemia results from the physical aggregation of the hemoglobin protein constituent in red blood cells. This aggregation results in a distortion in shape of deoxygenated red blood cells and causes impairment of flow of the blood through the capillaries (sickle cell "crises"). As the principal function of hemoglobin is to transport oxygen from the lungs to body tissues, efficient flow of oxygen throughout the body's tissues is impeded by the anemia due to a lower number of red blood cells. Sickle cell anemia also may have an indirect effect on the heart, lungs, kidneys, spleen, hips and brain. Sickle cell anemia crises can be extremely painful, can result in infections such as pneumonia, can result in skin ulceration, can contribute to strokes and seizures in the one afflicted and can also result in the development of chronic bone infections.

In general, the result of the differences between cells containing hemoglobin A, the normal hemoglobin, and hemoglobin S, the sickle cell hemoglobin, is that the former cell is generally flexible and bioconcave discoid in shape while the latter is more rigid and crescent shaped and typically has pointed ends. This rigidity and distortion in shape cause the cells to be lodged in the capillary. Hemoglobin molecules contain two beta polypeptide chains and two alpha polypeptide chains. In the sickle cell hemoglobin, a mutation is present in the beta chains. More specifically, the sixth amino acid of each beta chain is changed from glutamic acid to valine. As a result of this mutation, hemoglobin S upon deoxygenation polymerizes and causes the cell to assume the elongated, sickle-like configuration. As the sickle cells have a much shorter life span than normal red cells, the effect on the body is to deplete the total volume of blood cells thereby creating an anemic condition.

To the best of applicant's knowledge there has been no known effective means of arresting sickle cell anemia so as to prevent an individual who has this malady from experiencing one of the above-described problems. One known laboratory test employed in diagnosing sickle cell anemia is the performance of a hemoglobin electrophoresis test which is used to determine whether an individual has sickle cell anemia (homozygous) or merely the sickle cell trait (heterozygous), with the latter referring to an individual not having the disease but having the capability of transmitting the disease to offspring if mated to another heterozygote. Treatment for the various complications which have resulted from sickle cell anemia are known and should be distinguished from prophylactic activity (unknown) which would resist the occurrence of the complications. Currently, only symtomatic treatment is available. For example, people can treat the symptoms by using analgesics for pain, and antibiotics for infection, but these approaches do not arrest the sickling phenomena.

There remains, therefore, a very real and substantial need for a method of minimizing the adverse consequences of sickle cell anemia through resisting sickle cell crises in an individual who has this abnormality.

SUMMARY OF THE INVENTION

The present invention has met the above-described need by providing a method which involves administering to a person a therapeutically effective dosage of the compound

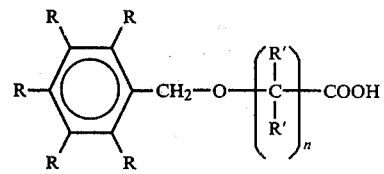

wherein at least one R=Cl, Br, CH$_3$ or OCH$_3$ and all the remaining R=H, R$^1$=H or CH$_3$ and n=1, 2, 3, 4, or 5. Where more than one R is selected from the group consisting of Cl, Br, CH$_3$ and OCH$_3$ (a) individual members of the group may be repeated or (b) combinations of the individual members or (c) both may be used. For example, methyl may be provided at two positions or methyl may be provided at one position and chlorine or bromine at another. Among the preferred materials for use in this process are p-bromobenzyloxyacetic acid, 2-(p-bromobenzyloxy)-2-methylpropionic acid and 3, 4 dichlorobenzyloxyacetic acid. The compound is preferably administered orally, as by solid dosage form such as a capsule. The method may advantageously be employed as a prophylactic means of resisting a sickle cell crisis in a sickle cell anemia patient.

The present invention also provides the compound 2-(p-bromobenzyloxy)-2-methylpropionic acid and the compound, 3, 4 dichlorobenzyloxyacetic acid and a pharmaceutical in unit dosage form having either of these compositions. The compound has properties of resisting the aggregation of hemoglobin in a sickle cell anemia patient.

It is an object of the present invention to provide a method of treating a sickle cell anemia patient so as to reduce undesired sickle cell crises and a compound usable for such purpose.

It is another object of the present invention to provide an effective means through both method and an associated compound for resisting undesired sickling of hemoglobin in sickle cell anemia patients.

It is a further object of the present invention to provide such a method and an associated compound which may readily be used without great inconvenience to the patient.

These and other objects of the invention will be more fully understood from the following description of the invention on reference to the illustrations appended hereto.

DESCRIPTION OF THE PREFERRED EMBODIMENTS

In the preferred method of the present invention a sickle cell anemia patient is administered a therapeutically effective dosage of the compound

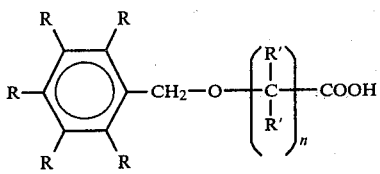

wherein at least one R=Cl, Br, CH₃ or OCH₃ and all the remaining R=H, R¹=H or CH₃ and n=1, 2, 3, 4 or 5.

Among the specifically preferred compounds for use in this method are compounds selected from the group consisting of p-bromobenzyloxyacetic acid, 2-(p-bromobenzyloxy)-2-methylpropionic acid and 3, 4 dichlorobenzylacetic acid. The first compound is illustrated adjacent "(a)" below and the second compound is illustrated adjacent "(b)" and the third "(c)".

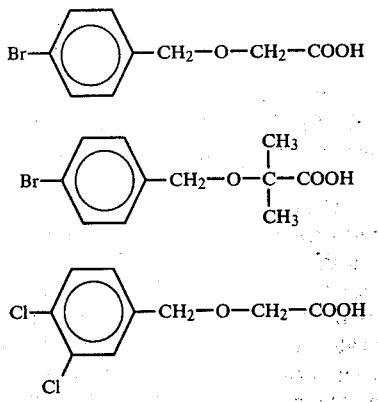

While p-bromobenzyloxyacetic acid (a) is a known compound and the method of preparing the same is known, (See Andre Viout and Henry Goult, Compt. rend., 237, 1162-4 (1953), a process of preparation will be disclosed herein.

In this process, 1.87 gm (0.01 mole) of p-Bromobenzyl alcohol was dissolved in 35 ml dry tetrahydrofuran (THF). To this solution, 0.48 gm of sodium hydride 50% oil dispersion (0.01 mole) was added slowly with stirring for ½ hour. In another flask 1.85 gm (0.01 mole) of iodoacetic acid was dissolved in 35 ml dry THF, and 0.48 gm of sodium hydride oil dispersion (0.01 mole) was added slowly with stirring for 15 minutes or until hydrogen evolution ceased. The sodium salt of the alcohol was added to the sodium salt of the acid portion with continuous stirring. The mixture was refluxed with stirring for five hours. After this the solution was allowed to cool and extracted with 100 ml cold water (all the solid precipitated during the reaction dissolved). The aqueous solution was next extracted with 20 ml CHCl₃ to remove any unreacted p-bromobenzyl alcohol and oil liberated from sodium hydride dispersion. After concentration of the remaining aqueous layer by evaporation to 50 ml, it was cooled, acidified with cold concentrated HCl and placed in an ice bath to solidify any oily material that formed. This produced a solid product which was filtered and recrystallized from 100 ml of boiling water. The yield was 1.7 gm (70% of the theoretical amount) with m.p. (79°-80° C.).

A method of preparing 3, 4-dichlorobenzyloxyacetic acid (c) is as follows. In this process, 1.77 gm (0.01 mole) of 3,4-dichlorobenzyl alcohol together with 1.39 gm (0.01 mole) bromoacetic acid were dissolved in 30 ml dry THF. 0.96 gm (0.02 mole) of sodium hydride 50% oil dispersion was added cautiously with stirring. The mixture then was refluxed with continuous stirring for six hours, THF was removed by rotary evaporation and 60 ml of water was added to the mixture. This aqueous extract was extracted with 20 ml CHCl₃, then concentrated to half its volume, cooled in an ice bath, poured into a mixture of 5 ml 50% H₂SO₄ and 20 gm ice. After the ice melted the product was filtered, and recrystallized from boiling water (50 ml). The yield was 0.8 gm (33% of the theoretical amount) with m.p. 58°-60° C.

The following method is suitable for preparing 2-(p-bromobenzyloxy)-2-methylpropionic acid (b). In this process, 2.08 gm of 2-hydroxyisobutyric acid (0.02 mole) was dissolved in 30 ml of dry THF, then 1.92 gm (0.04 mole) of sodium hydride dispersion in oil was added gradually with stirring until hydrogen evolution ceased (about ½ hour). A solution of 5 gm (0.02 mole) of p-bromobenzyl bromide in 30 ml dry THF was dropped into the above-prepared disodium salt of the acid (addition took about 30 minutes) with continuous stirring. This mixture was refluxed for seven hours, cooled and extracted with 50 ml H₂O. The aqueous solution was extracted with 20 ml CHCl₃ and aqueous concentrated by evaporation, cooled and acidified with concentrated HCl. The resultant material was cooled in an ice bath to solidify any product that separates as oil, filtered and recrystallized from boiling water. m.p. 111°-113° C. yield, 1.7 gm (31% of the theoretical amount).

Anal. calcd for $C_{11}H_{13}O_3Br=C$, 48.35; H, 4.73; Br, 29.30; Found=C, 48.47, H, 4.90; Br, 29.16.

Mass spectrum: calcd. for $C_{11}H_{13}O_3Br^{79}$, 272.0048; Found: 272.0029.

EXAMPLE

In order to confirm the effectiveness of these compounds in reducing the effect of sickle cell anemia, tests were performed. The materials were tested according to the assay developed by Hofrichter et al. (J. Hofrichter, P. D. Ross and W. A. Eaton, Proc. Natl. Acad. Sci., USA, 73 30-35, 1976). This assay involves deoxygenation of concentrated sickle hemoglobin with dithionite in the presence of different concentrations of the drugs being tested. Samples are then sealed in quartz epr tubes under anaerobic conditions and spun at about 150,000 x g for about 2½ hours at about 35° C. in an ultracentrifuge. This procedure pellets the polymerized HbS (sickle hemoglobin) to the bottom of the tubes and the supernatant (soluble HbS) is measured in the laboratory as the cyanmethemoglobin derivative. The more active the compound the greater the solubility of HbS and the smaller the pellet size. Activity is reported as a ratio of the HbS solubility with the particular drug to HbS solubility with no drug i.e. control. The higher the ratio the greater degree of activity of the drug.

The results of these tests are shown in table 1.

TABLE 1

| Drug Conc. | I | II | III |
|---|---|---|---|
| 5 mM | 1.059 | 1.048 | 1.100 |
| 10 mM | 1.118 | 1.086 | 1.176 |
| 20 mM | 1.233 | 1.193 | 1.320 |
| 40 mM | 1.398 | 1.379 | 1.371 |

In Table 1 the ratios for p-bromobenzyloxyacetic acid (a) (Column I), 2-(p-bromobenzyloxy)-2-methylpropionic acid (b) (Column II) and 3,4 dichlorobenzyloxyacetic acid (c) (Column III) are shown. It will will be noted that the ratios needed for a clinically less severe condition (S/B+ thal to HbS/S (1.06–1.17)) are reached with the use of these three compounds at as low as 5 to 10 mM (1.059 to 1.176). In these tests the average HbS concentration was around 3.7 mM. This indicates that only about two moles of the drug are needed for every mole of HbS in order to effect polymerization significantly. In red blood cells, the concentration of Hb is usually around 5 mM and with a typical hematocrit for homozygous S/S patients of 30%, the concentration of Hb in whole blood is approximately 1.5 mM. Therapeutically then, these compounds are within the dosage range needed for positive clinical effects.

In order to evaluate the significance in respect of antigelling results of the drugs tested with respect to possible clinical significance, published solubility ratios and kinetic parameters (under these assay conditions) for correlation of clinical severity with inhibition of sickle cell gellation were considered. See H. R. Sunshine, J. Hofrichter, W. A. Eaton, *Nature,* 275, 238 (1978). These authors report the solubility ratios which result from mixtures of HbS and fetal hemoglobin (HbF) and HbS and HbA. In the double heterozygous conditions of S/B+ thalassemia (15–30% HbA), which are clinically somewhat less severe than homozygous HbS disease, ratios of HbS/B+ thal to HbS/S range from 1.06 to 1.17. For conditions which are much less severe, as in the double heterozygous condition of sickle/hereditary persistance of fetal hemoglobin (S/HPFH) in which red cells contain about 20 to 30% hemoglobin F, the solubility ratios obtained (HbS/HPFH) to HbS/S range from 1.19 to 1.26.

In general, it is preferred that the compound be taken orally and in solid dosage form, as in a capsule, for example. It is preferred that the daily dosage be about 1 to 4 grams per day.

The present invention also provides the new compounds 2-(p-bromobenzyloxy)-2-methylpropionic acid and 3, 4 dichlorobenzyloxyacetic acid. These compounds may advantageously be provided in unit dosage pharmaceutical form. It has the advantageous properties of resisting aggregation of hemoglobin in people having sickle cell anemia.

It will be appreciated that the present invention provides both a compound and a method for treatment for sickle cell anemia patients so as to resist undesired sickle cell anemia crises. The method and compound may advantageously be employed as a prophylactic.

Whereas particular embodiments of the invention have been described above for purposes of illustration, it will be evident to those skilled in the art that numerous variations of the details may be made without departing from the invention as defined in the appended claims.

I claim:

1. A method of treating a person for sickle cell anemia including orally administering to said person a therapeutically effective dosage of the compound

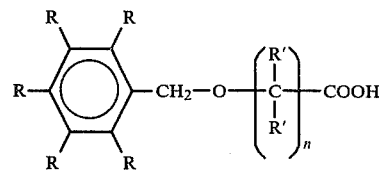

wherein at least one R=Cl, Br, CH$_3$ or OCH$_3$ and all the remaining R=H, R$^1$=H or CH$_3$ and n=1, 2, 3, 4 or 5.

2. The method of claim 1 including providing the compound from the group consisting of p-bromobenzyloxyacetic acid, 2-(p-bromobenzyloxy)-2-methylpropionic acid and 3,4 dichlorobenzyloxyacetic acid.

3. The method of claim 2 including administering said compound in solid dosage form.

4. The method of claim 3 including administering said compound in capsule form.

5. The method of claim 3 including administering said compound at a dosage rate of about 1 to 4 grams per day.

6. The method of claim 1 including administering said compound as a prophylactic means to resist a sickle cell crisis.

7. The compound 2-(p-bromobenzyloxy)-2-methylpropionic acid or 3,4 dichlorobenzyloxyacetic acid.

8. The compound of claim 7 provided as a pharmaceutical in orally administrable solid unit dosage form, and said compound has properties of resisting sickling of hemoglobin in a sickle cell anemia patient.

* * * * *

UNITED STATES PATENT AND TRADEMARK OFFICE
CERTIFICATE OF CORRECTION

PATENT NO. : 4,482,571
DATED : November 13, 1984
INVENTOR(S) : Donald J. Abraham It is certified that error appears in the above-identified patent and that said Letters Patent is hereby corrected as shown below:

Column 4, line 9, "into" should read -- onto --.

Column 5, line 25, after "(HbF)", "and" should read -- or --.

Signed and Sealed this

Twenty-third Day of April 1985

[SEAL]

Attest:

DONALD J. QUIGG

Attesting Officer

Acting Commissioner of Patents and Trademarks